US011221323B2

(12) United States Patent
Chan et al.

(10) Patent No.: US 11,221,323 B2
(45) Date of Patent: Jan. 11, 2022

(54) SYSTEM AND METHOD FOR INSTANTANEOUSLY DETERMINING UNIFORM DISTRIBUTION OF WATER, SALINITY, CONDUCTIVITY, TEMPERATURE AND OTHER CONDITIONS IN SOIL

(71) Applicant: STEVENS WATER MONITORING SYSTEMS, INC., Portland, OR (US)

(72) Inventors: Chun Kit Chan, Clackamas, OR (US); Michael Kuvelas, Vancouver, WA (US); Carmen Magro, Wynnewood, PA (US); Scott South, Vancouver, WA (US)

(73) Assignee: Stevens Water Monitoring Systems, Inc., Portland, OR (US)

( * ) Notice: Subject to any disclaimer, the term of this patent is extended or adjusted under 35 U.S.C. 154(b) by 510 days.

(21) Appl. No.: 15/440,998

(22) Filed: Feb. 23, 2017

(65) Prior Publication Data

US 2017/0241973 A1    Aug. 24, 2017

Related U.S. Application Data

(60) Provisional application No. 62/298,886, filed on Feb. 23, 2016.

(51) Int. Cl.
*A01B 79/00* (2006.01)
*G01N 33/24* (2006.01)
(Continued)

(52) U.S. Cl.
CPC .......... *G01N 33/246* (2013.01); *A01G 20/00* (2018.02); *H04Q 9/00* (2013.01); *G08C 2201/93* (2013.01); *H04Q 2209/40* (2013.01)

(58) Field of Classification Search
CPC .. G01N 33/246; G08C 2201/93; A01G 20/00; A01G 22/00; H04Q 9/00; H04Q 2209/40
See application file for complete search history.

(56) References Cited

U.S. PATENT DOCUMENTS

4,192,510 A    3/1980  Miller
5,668,306 A    9/1997  Doherty et al.
(Continued)

*Primary Examiner* — Mohamed Charioui
*Assistant Examiner* — Christine Y Liao
(74) *Attorney, Agent, or Firm* — FisherBroyles LLP; Kevin D. Jablonski (57) ABSTRACT

A system and method for objective and real-time measurable indicator for calculating distribution uniformity of water, salinity, conductivity, or temperature in turf are disclosed. In one embodiment, a system and method may be directed to collecting turf condition data using a compact, portable turf analysis device having one or more sensors and Global Positioning System (GPS) module configured to collect location data to a server database. The server assimilates the turf condition data and location data into the server database to determine distribution uniformity of measurements and to calculate turf performance indicators of the turf conditions in a plurality of locations to determine turf performance, turf stress, and turf management best practices. By tracking and analyzing the turf condition data for one or more turf locations as well as location data, the turf quality is objectively measured and managed.

13 Claims, 5 Drawing Sheets

(51) Int. Cl.
*A01G 20/00* (2018.01)
*H04Q 9/00* (2006.01)

(56) References Cited

U.S. PATENT DOCUMENTS

| | | |
|---|---|---|
| 5,736,631 A | 4/1998 | Dixon et al. |
| 5,886,253 A | 3/1999 | Joustra et al. |
| D418,073 S | 12/1999 | Kreutzer et al. |
| 6,171,199 B1 | 1/2001 | Cohodas |
| 6,601,440 B1 | 8/2003 | Chuang et al. |
| 6,826,972 B2 | 12/2004 | Clark et al. |
| 7,106,076 B2 | 9/2006 | Tillmann et al. |
| D616,314 S | 5/2010 | Akomolede et al. |
| 8,656,759 B2 | 2/2014 | Hughes et al. |
| 9,952,327 B2 | 4/2018 | Schultz |
| 2005/0024213 A1* | 2/2005 | Franzen .............. A01D 34/006 340/600 |
| 2011/0203356 A1* | 8/2011 | Scherbring ............. G01N 3/40 73/84 |
| 2012/0084115 A1 | 5/2012 | Cline |
| 2012/0109387 A1 | 5/2012 | Martin et al. |
| 2013/0308426 A1* | 11/2013 | Scarlatti .................. G01V 1/16 367/129 |
| 2014/0035752 A1 | 2/2014 | Johnson |
| 2015/0309496 A1 | 10/2015 | Kah, III et al. |
| 2015/0323491 A1* | 11/2015 | Miller .................... G01N 33/24 205/789 |

* cited by examiner

SYSTEM AND METHOD FOR INSTANTANEOUSLY DETERMINING UNIFORM DISTRIBUTION OF WATER, SALINITY, CONDUCTIVITY, TEMPERATURE AND OTHER CONDITIONS IN SOIL

CROSS REFERENCES TO RELATED APPLICATIONS

The present application claims priority and benefit from the U.S. Provisional Patent Application No. 62/298,886, filed Feb. 23, 2016 and titled, "SYSTEM AND METHOD FOR INSTANTANEOUSLY DETERMINING UNIFORM DISTRIBUTION OF WATER, SALINITY, CONDUCTIVITY, TEMPERATURE, AND OTHER CONDITIONS IN SOIL". The entire content of the provisional application is herein expressly incorporated by reference. Further, the present application refers a commonly-assigned U.S. patent application Ser. No. 15/441,015, entitled "System and Method for Tracking and Optimizing Pinhole Locations on a Putting Green" filed on Feb. 23, 2017, and commonly-assigned U.S. patent application Ser. No. 15/441,023, entitled "System and Method for Detecting Turf Performance Indicators" filed on Feb. 23, 2017, the disclosures of which are incorporated by reference.

BACKGROUND

Golf is a sport enjoyed by millions of people the world over. Its popularity indicates that interest in golf remains vibrant and growing. As a result, golf courses and groundskeepers are always seeking to enhance the playing experience for golfers while increasing efficiencies in maintaining fairways and putting greens. Many variables may affect turf quality including water absorption, water retention, soil content, salinity influences, weather, and use patterns. Thus, groundskeepers are continuously monitoring various conditions in an effort to maintain or improve the quality of the turf in fairways and greens.

One particular area of which groundskeepers are keenly aware of involves water absorption and distribution both on putting greens and in fairways. Historically, a mechanical way to determine how much water may be distributed in various areas is to use a grid of catch-cups at surface grade level to capture water as it fell to the turf. This time consuming manual process proves to be problematic as the method assumes that all turf is equally absorbent with uniform qualities, and assumes other environmental variables do not influence the consistent distribution of water from a rain event or irrigation system. In addition to water distribution in soil, there is no efficient method of measuring the soil distribution impact from fertilizer, nutrient, or soil conditioning applications. In reality, different areas behave differently at different times. Thus, groundskeepers typically hone their craft through years of trial and error experience such that a feel for the turf may be developed. Of course, the "feel" may differ from course to course and from groundskeeper to groundskeeper. Conventional golf course maintenance does not have any objective, real-time measurable indicator for actual distribution uniformity of water, salinity, conductivity, or temperature in soil.

BRIEF DESCRIPTION OF THE DRAWINGS

Aspects and many of the attendant advantages of the claims will become more readily appreciated as the same become better understood by reference to the following detailed description, when taken in conjunction with the accompanying drawings, wherein:

Note that the same numbers are used throughout the disclosure and figures to reference like components and features.

DETAILED DESCRIPTION

The subject matter of embodiments disclosed herein is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Embodiments will be described more fully hereinafter with reference to the accompanying drawings, which form a part hereof, and which show, by way of illustration, exemplary embodiments by which the systems and methods described herein may be practiced. The systems and methods may, however, be embodied in many different forms and should not be construed as limited to the embodiments set forth herein; rather, these embodiments are provided so that this disclosure will satisfy the statutory requirements and convey the scope of the subject matter to those skilled in the art.

By way of overview, the subject matter disclosed herein may be directed to systems, apparatuses, and methods for using a turf analysis device for determining various factors and variables in turf across one or more turf locations. From the collected data, an algorithm is performed that calculates the average of the measurements in the lowest 25% of the collected data, and then divides this number by the average of the measurements in all collected samples. This algorithm is commonly known as the "Low Quarter Distribution Uniformity Method", and the resulting value is expressed in a distribution uniformity percentage for the sampled location. The physical sample process of this method involves data samples every 10 foot on a green or 30 foot center on fairways. This "Low Quarter Distribution Uniformity Method" and related sampling process has been historically used to determine the distribution uniformity of water from an irrigation system based on the catch-cup method previously described. One embodiment enhances and expands this historical catch-cup method to a more relevant, timely, and precise measurement of water distribution uniformity in the soil by incorporating the same historical calculations and process using a compact, portable turf analysis devices and system that automatically calculates the distribution uniformity in soil in real-time without the manual process involved with the traditional catch-cup system. In addition, simultaneously to water distribution uniform calculation, one embodiment also calculates the distribution uniformity of conductivity, salinity, and temperature in the soil for a user defined area. In other calculation and process a factor of distribution uniformity that is unique uses the Turf Performance Indicator in determining an optimal value.

For example, instead of the Distribution Uniformity being at 80% or better based on the "Low Quarter Distribution Uniformity Method", a TPI that incorporates other Instead of DU being good at 80% or better, an embodiment may calculate a TPI integrated with uniformity analysis in addition to other relevant variables uses in the TPI formula to identify a value of say 85 or better (or 8.5 on a 10 point scale) to Another alternative distribution uniformity assessments may include a standard deviation calculation for a set of data samples and compare such value to user defined tolerances. Further lab analytics and additional algorithms for assessing specific factors of turf may be implemented based on the initial collected data. All data may be assimilated into a database and compared against previous data collections from earlier in time as well as previous collections of data from other locations of turf. By developing one or more repeatable and reliable indicators of soil measurement conditions uniform distribution indicators, a groundskeeper may implement specific factor-based solutions to improve irrigation system coverage and fertigation practices. These and other advantages will become more apparent in the detailed descriptions below with respect to FIGS. 1-5.

Figure 1:
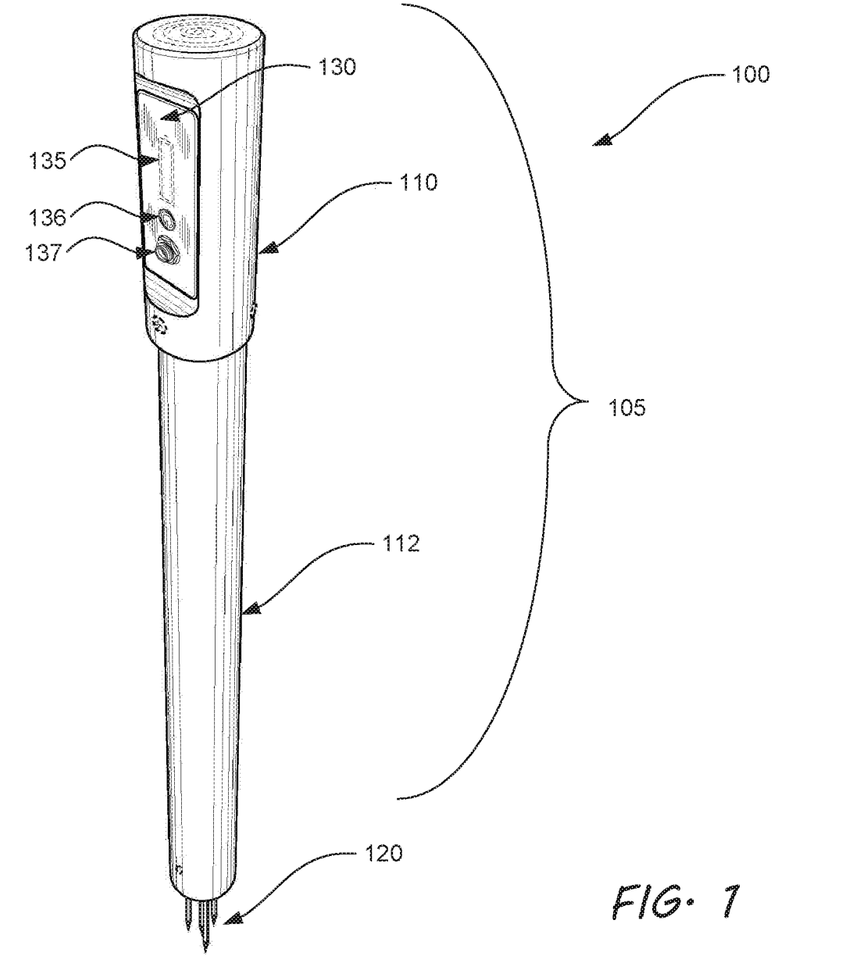
FIG. 1 is a device for performing turf analysis according to an embodiment of the subject matter disclosed herein.

FIG. 1 is a diagram of a turf analysis device for performing uniform distribution analysis of soil water, soil conductivity, soil salinity, soil temperature, and other soil conditions for turf locations according to an embodiment of the subject matter disclosed herein. The device 100 may be embodied in an elongated housing 105 that may be cylindrical in nature. The housing 105 may include an upper portion 110 that is slightly larger in circumference than a lower portion 112. Below the surface of the tube 112 is a rechargeable battery for providing power to the device 100. The lower portion 112 may also be tapered. The housing may have a length of between six inches and three feet.

The housing includes four prongs 120 at a bottom end of the lower portion 112. The four prongs 120 include a pointed end designed to penetrate the surface of turf, such as a putting green or a fairway. The prongs may be conductively coupled to integrated electronics (not shown in FIG. 1) in the interior of the device 100. The prongs coupled with integrated electronics becomes a multi-parameter research grade sensor to determine specific physical aspects of the turf, such as water content, conductivity, salinity, temperature, and the like. Using a research grade sensor that provides consistent measurement using any number turf analysis devices is important for a uniform distribution assessment based on sample data from different turf analysis devices 100. For example, soil moisture percentage measurement of 22% using one turf analysis device should be approximately the same measurement using any number of other turf analysis devices. When the prongs 120 are engaged with the turf, the device 100 may stand upright on its own.

The upper portion 110 may include a flat area 130 that contains various input and output functionality for the device. The flat area 130 may include a removable cover for engaging or disengaging an underlying battery (not shown), a communication module 220, a processor 210, and a GPS module 225 (all shown in FIG. 2).

The flat area 130 may, in and of itself, be a display 135 (such as an LED display, for example) for displaying data such as the data being collected. The display 135 may show additional data such as coordinates of the current location and battery life remaining. The flat area 130 may include a software-based or hardware-based power button 136 for turning the device 100 on and off. The flat area 130 may include an interface 137 for recharging the battery. Additional features of the device 100 are shown in the block diagram of FIG. 2.

Figure 2:
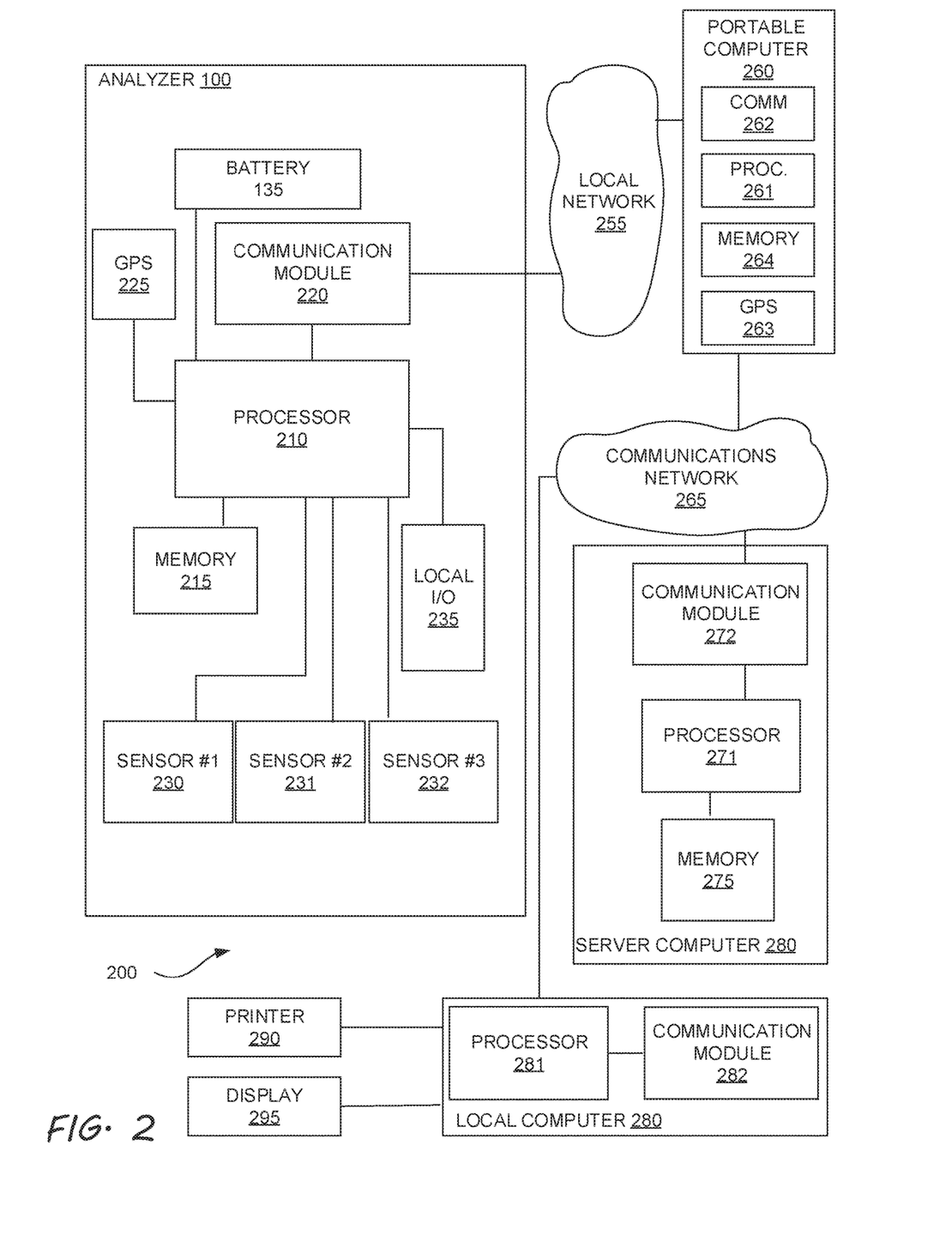
FIG. 2 is a system for using the turf analysis device of FIG. 1, according to an embodiment of the subject matter disclosed herein.

FIG. 2 is a system 200 for using the turf analysis device 100 of FIG. 1, according to an embodiment of the subject matter disclosed herein. The system 200 includes the turf analysis device 100, a local portable computing device 260 and a server computer 270, and a local computer 280 that may be coupled to an external display 295 and a printer 290. As briefly mentioned previously, the turf analysis device 100 includes a processor 210 and a local memory 215 that may store instructions that may be executed by the processor 210. Further, local 1/O 235 is coupled to the processor 210 and may be a power button or a display as discussed above. The processor 210 and other components may be coupled to the battery 135 for provision of power.

In this embodiment, there are three sensors 230, 231, and 232 shown but there may be more or fewer depending on application and model. The sensors 230, 231, and 232 may include probes, embodied in the prongs 120 of FIG. 1 for engaging with turf surface and soil below surface of turf. The multi-parameter sensor may include a soil analysis sensor, and electric conductivity sensor, a soil moisture sensor, soil salinity sensor, a temperature sensor, or any other sensors that may be useful in determining data about soil or turf. Other measurements that may be used in determining influence on distribution uniformity and turf quality include slope, soil type, grass type, root depth of grass, turf compaction and firmness, weather conditions, seasonality, or sun exposure. The turf analysis device 100 includes various interfaces for engaging exterior computer networks. A first interface is a communication module 220, which may be communicatively coupled to communication module 262 for providing a communication link between the turf analysis device 100 and one or more remote computing devices, such as portable computer 260. In one embodiment, the communication modules 220 and 262 may be wireless network adapters for WiFi interconnectivity using IEEE-802.xx standards and TCP/IP protocol. In other embodiments, the communication modules 220 and 262 may be short-range network modules for using BlueTooth™ and the like. In still further embodiments, the communication module 262 may be a cellular network device for engaging one or more Long-Term Evolution (LTE), e.g., cellular, networks. These communication modules 220 and 262 may communicate through a local communication network 255 as discussed in the embodiments above.

Another interface for engaging another computer network is Global Positioning System (GPS) module 225. The GPS module 225 may be configured to engage the GPS whereby a space-based navigation system provides location, altitude, and time information in all weather conditions anywhere on or near the Earth when the device can connect to a computer network where there is an unobstructed line of sight to four or more GPS satellites determining location. The GPS module 225 may link directly to the GPS satellite network or may link to other networks (such as an LTE network). The GPS module 225 provides data, typically in the form of longitudinal and latitudinal coordinates as well as altitude in terms of distance from sea level. The GPS data may be assimilated with sensor data by the processor 210 and then communicated via the communication module 220 to the local remote portable computer 260. The GPS data may also be assimilated by portable computer 260 that have integrated GPS module 263.

The portable computer 260 may be any number of mobile computing devices such as a smart phone, a tablet, a laptop computer and the like. The portable computer 260 may typically include one or more local processors 261, communications modules 262, and memories 264 for sending, receiving and storing data as well as execution applications. A local memory 264 may store instructions that may be communicated to and executed by the processor 210 at the turf analysis device 100. The portable computer 260 may also include an integrated GPS 263 battery (not shown), and display (also not shown). The memory 264 may also store data collected by various sensors such as sensors 1-3 230, 231, and 232; data collected from the GPS module 225 or 263; and battery health conditions. In the system 200 of FIG. 2, the portable computer 260 may be configured to execute a pinhole tracking and optimization application to be used in conjunction with the turf analysis device 100. The pinhole tracking and optimization applications are described in commonly-assigned U.S. patent application Ser. No. 15/441,015, entitled "System and Method for Tracking and Optimizing Pinhole Locations on a Putting Green" filed on Feb. 23, 2017, the disclosure of which is incorporated by reference.

The distribution uniformity analysis application may track and locally store data (in memory 264) about measurements of soil water, soil conductivity, soil salinity and soil temperature and link GPS location to the application using an integrated GPS module 225 or application for wirelessly linking to a more accurate GPS location device. The application may be configured to log measurements of soil water levels, soil conductivity, soil salinity and soil temperature at locations and automatically link such location information to a centralized software program. In addition to these logged measurements, logged information may also include date, time, latitude, longitude, altitude, picture and/or electronic notes inputted by user for each location. The application may also track historical trending of sensor measurements and of pinhole location per a golf green. Such historical location information is selectable by user. The application may be configured to guide and warn a groundskeeper of optimal irrigation settings, fertilization applications, and soil treatment additives. Further, the application provides a means for real-time calculations and reporting of distribution uniformity of soil water levels, of soil salinity levels, of soil conductivity levels, and of soil temperature for selected zones that may be used to improve management of turf quality and conditions. There are a variety of conditions that may influence the uniformity of soil abortion of water and nutrients. Such conditions using catch-cup historical manual irrigation distribution uniformity calculations are not addressed on a timely basis and often not addressed at all. For example, unexpected blow outs in irrigation pipes and malfunctioning sprinklers are inevitable events that contribute to inconsistent water output. Water pressure in an irrigation system may change often. As system materials age they become less reliable due to worn out nozzles and gaskets, inevitable leaks, and clogged emitters. Salts in soil can accumulate and nitrogen can leach, which adversely impact the quality of the turf or crop even with uniformed water distribution. Irrigation water with high salinity content can adversely impact the turf quality. Other factors such as windy days can widen the throw of impact sprinklers. Slope can influence the uniformed absorption of water and nutrients in the soil. Because distribution uniformity of water, conductivity, salinity and temperature in the soil has significant impact on turf quality and health, running on-going, real-time distribution uniformity calculations of these measurement in the soil will lead to optimal best management practices of water usage, fertilization practices, and soil amendments to optimize the health and quality of the turf.

Upon collection of enough historical data, the application may be used to animate water distribution levels, soil salinity levels, soil conductivity levels and soil temperature over user defined data history that is viewable on-line via software as a service platform. Further, the measurement levels may be overlaid on a Geographic Information System (GIS) location satellite image with various selectable layers for visual analysis.

The system 200 may further include a server computer 270 for storing data collected remotely and for assimilating soil moisture, soil salinity, soil conductivity, and soil temperature conditions to determine uniformity of these conditions over a defined area instantaneously and over the course of time. The server computer 270 may be communicatively coupled to the portable computer 260 and to a local computer 280 through various means using the communication network 265. Thus, the application(s) discussed above may be cloud-based utilizing a server processor 271 having a local memory 275 through a local communications module 272.

The system 200 may include a printer 290 interfaced with the local computer 280 for printing water, salinity and temperature distribution uniformity information and maps. One or more application may include a printing program that is linked to each golf course golf hole and respective golf green pinhole locations based on the most recently logged GPS location. Further, additional data may be printed on a golf card or displayed at the display 295 such as historical pinhole locations and respective effects on handicap, players' names, players' handicaps, marketing information from the golf course, current weather conditions and forecast, and the like. The applications discussed above may utilize a server processor 281 and a local communications module 282 within the local computer 280.

Figure 3:
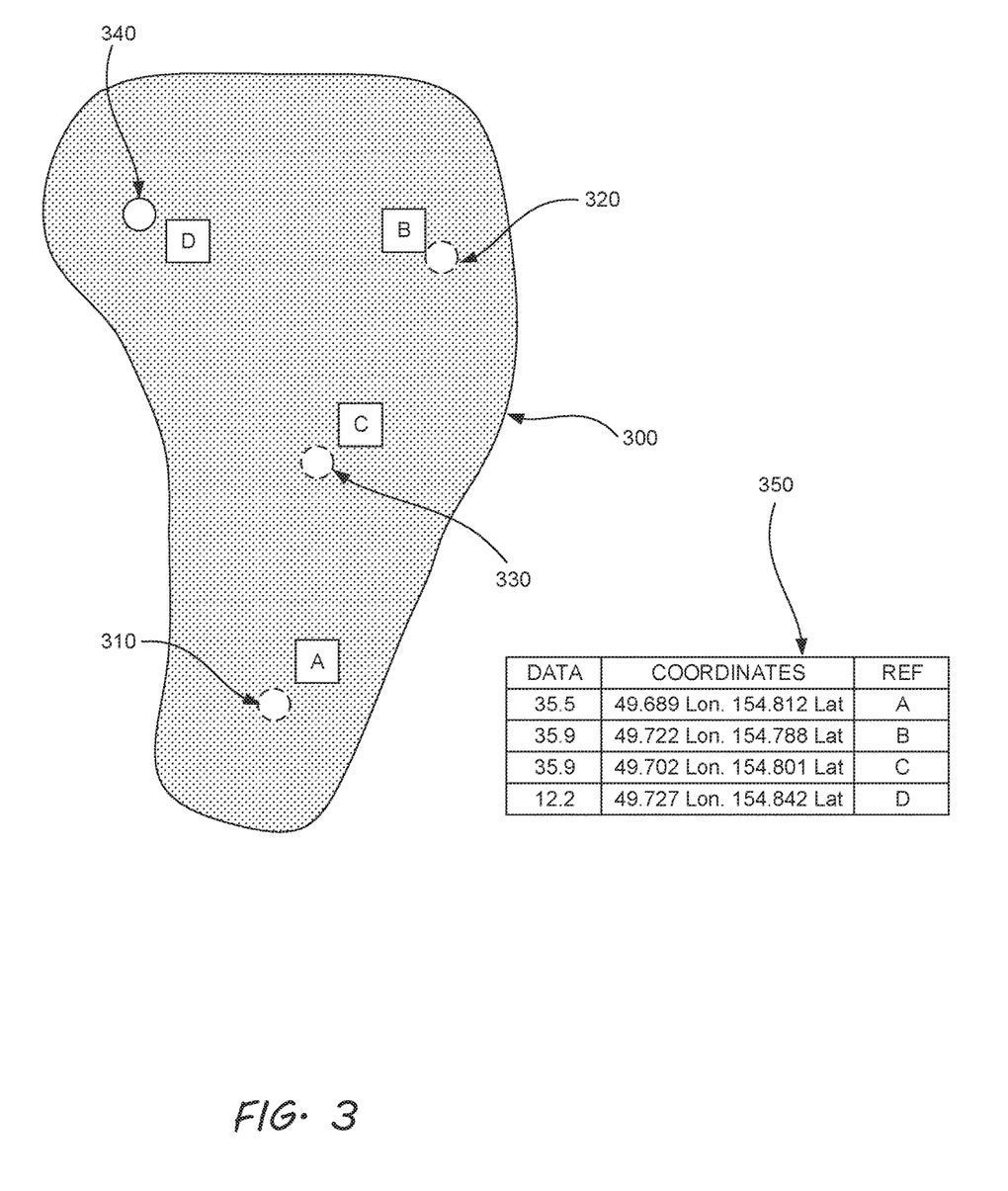
FIG. 3 is a diagram illustrating a screen shot showing a putting green 300 having various turf analysis locations along with turf analysis data according to an embodiment of the subject matter disclosed herein.

FIG. 3 is a diagram illustrating a putting green 300 having various turf analysis locations along with turf analysis data according to an embodiment of the subject matter disclosed herein. Such a view may be displayed on a display at any computer such that a user may utilize and interact with data collected and to be collected by a turf analysis device 100. In this illustration, a putting green 300 is shown, however, any depiction of turf may be rendered such as a fairway, sports field, or even a simple block diagram showing regions of turf to be analyzed. Further, the putting green shows four turf analysis locations. There may be many more in a typical analysis, but four are illustrated here for the purposes of this embodiment. The four locations correspond to references A 310, B, 320, C, 330, and D 340. The locations may correspond to actual locations in which the turf analysis device 100 was used to determine specific factors (e.g., data collected) about the turf. These factors may be assimilated into a local or remote database to be used for soil water, conductivity, salinity, and/or temperature measurements in a distribution algorithm (discussed below) to determine an overall respective distribution. Each measurement indicator for each analysis location may be displayed in a table 350.

Measurements of soil water, conductivity, salinity and/or temperature distribution level at each location, in and of itself, may be the result of several factors. The factors may be determined using a turf analysis device 100 within a turf and soil insight system. The collection of data about the various factors makes it possible to effectively measure key variables that indicate distribution uniformity of soil measurements, turf performance, and turf stress to be assessed for current and/or trending conditions. In addition, lab analytics can be used to indicate key characteristics that become additional indicators when combined with in situ measurements of key variables of the turf. In an effort to assess the distribution uniformity of any turf system soil measurements, one may measure several stresses individually and tailor lab analytics to include key assessments associated with understanding what monitored measurements mean as far as their insight to true uniform distribution conditions.

Once several different locations in a particular area have been analyzed, an application may assemble the collected data to generate a distribution table such that a user may see areas where the respective measurement level is greater and areas where such measurement level is lower. If the data point locations are all taken in proximate time with respect to each other, the relative soil water, soil conductivity, soil salinity or soil temperature measurements at each location do not matter in the context of such measurements with respect to each other. That is, the distribution analysis may focus on the relative differences from location to location. As such, whether or not turf was just under sprinklers or the area is experiencing a drought, the respective measurement's distribution can be determined as all locations have experienced the same external conditions.

The data may be further analyzed with respect to a span of time as different conditions will present depending on when the data is collected. For example, a first set of data may be collected in the spring. A next data set may be collected in the summer. A next set of data may be collected in the fall at night. Then all data may be assimilated and used to assess overall water distribution across all analysis locations for a given area (such as hole 18 or the back nine) across different seasons.

Further, soil water, soil conductivity, soil salinity and soil temperature measurements determined at each analysis location may be part of a larger more enveloping assessment of overall turf performance. Thus, one or more of these measurements may be one factor used when determining an overall turf performance indicator. In one embodiment, an algebraic equation may be used to assess the performance of a turf system against any one turf stress. Such an equation yields a Turf Stress Indicator (TSI). Further, using a weighted formula, one may combine the effects of several stresses to indicate a Turf Performance Indicator (TPI), which is an indication of turf performance as a whole.

The following paragraphs discuss the aspects of an overall TPI that may be the focus of one or more other related and concurrent patent applications.

The formulas are written to allow for the optimum levels to be customized while taking into account tolerance factors for each variable. The data collected may be assimilated into an analysis application to keep track of real time measurements using one or more stationary sensor systems. Further, the application may assimilate data collected from a measured variable or ratio of variables captured from portable monitoring, in-ground monitoring, lab analysis, or observational measurements that are made scientifically and practically.

The individual TSI calculation can be applied to any number of variables that can be recorded from the turf analysis device 100, the turf analysis weather station, soil sensors, lab analysis reports, and any other variable where a comparison of the actual versus the optimum can be made. The formula takes into account several factors that influence turf performance.

The Turf Stress Indicator (TSI) calculation for a single variable is $TSI=100/[(e^{0.5} (x-xo/TOL)^2)]Var1$ In this formula, the variables are: TSI=Turf Indicator Indicator where 100 is the least likelihood for the particular stress, 0 is the highest likelihood. The TSI may be thought of as the turf's strength against a particular stress. So a score of 100% means the turf is likely not under any pressure from that stress, or variable.

Another variable is e=mathematical constant of 2.71828 which is approximately the base of the natural logarithm. Another variable is x=measured variable of interest (moisture, salinity, temperature, EC/Moisture ratio, and the like). Another variable is xo=optimum value for the variable of interest (user definable and determined from a large network of users and collected data, customizable per customer's tolerances and key property or zone attributes determined from observations or lab analysis). Another variable is TOL=a defined tolerance factor for each measureable variable essentially defining the delta around an optimum value (i.e. if optimum salinity is 0.21 dS/m and it is desired to allow a range of 0.15 to 0.27, our TOL would be 0.12). Again, this is customizable and unique.

In a spreadsheet, the formula will look like that below and will not only calculate the TSI but will indicate whether the value is below (indicated by a negative value) or above the optimum level. This is important for several variables. For instance, if moisture has a 70% stress performance score, it may be important to know if it is too moist (positive value) or too dry (negative value) causing this less than optimum condition.

$$TSI(\text{Excel Language}):=(100/2.71828^{\wedge}(0.5*((B3-A3)/C3)^{\wedge}2))$$

Where:
B3 is a column assignment for measured condition
A3 is the column assignment for the optimum condition
C3 is the column assignment for the TOL factor
To determine whether the value is to the positive or negative size of optimum, a reference to the actual measured value minus the optimum value is made before combining the +/−symbol to the calculated TSI Value.

$$\text{Positive or Negative}(+/-)\text{value determination}(\text{Excel Language}):=\text{IF}(B3-A3<0,"-","+")$$

Where:
B3 is the column assignment for the measured condition
A3 is the column assignment for the optimum condition
Note that '+' is assigned to 0 values and above and '−' values are assigned to <0 values.

Turf Performance Indicator (Moisture, Salinity (EC), Canopy Temperature)

To truly calculate the performance of a turf system, several factors may be considered. For instance, if there is a moisture stress with limited salinity (EC) stress, then one level of turf performance exists. If there is the same turf system with low moisture stress but increased salinity stress, then another turf performance condition exists. If there are elevated moisture and salinity stresses, then an entirely different turf performance level exists. This can be the case for any number of variables. The three most easily ascertained and which are three of the most influential variables on turf performance include moisture, salinity (EC) and temperature. Further, with regard to temperature in particular, turf canopy, or surface temperature is a direct measurement of temperature's influence on turf stress. The turf analysis device 100 directly measures these variables using a research grade sensor requiring no calibration in any turf/soil type. This makes the repeated capturing of these variables easy and applicable to apply these calculations to understand how well the turf system is performing at any given time.

However, even when measured variable conditions are optimal, turf performance can be suffering from external influences not directly measurable. For example, pathogenic fungi can be invading a particular turf plot and causing disease decline even when temperature, moisture and salinity measurements are not indicating there is a problem. Pathogenic fungi are influenced by increased heat and moisture, but the attack on turf plants is not necessarily increased due to this. The recovery of the turf, however, is, in fact, directly related to the turf's performance at the time of disease onset. Therefore, having a knowledge of turf performance or having a quantitative value to associate with a qualitative condition has application in disease likelihood assessment or any other ailment that can result in turf decline.

Despite this fact that problems can still occur even when conditions seem optimal for good turf performance, using a customized visual analysis of the conditions may allow the input of a number indicating such visual appearance into the turf performance Indicator calculation allowing for a measurement of the overall turf performance to include a visual inspection. Generally speaking, however, when the TPI is high (>85%), turf performance is generally acceptable and least likely to develop conditions leading to declined performance.

By combining several Turf Stress Indicator results with weights to their influences applied, a weighted average Turf Performance Indicator can be calculated. Using a weighted average formula where this formula above would be calculated for any number of variables (i.e. salinity, moisture, temperature, ambient temp/humidity, traffic, etc.) and each of those variables are assigned a weighted value from 1 to 5 for instance, a summation of the result of multiplying each individual TSI by the weighted value and then dividing that total by the sum of all of the weighted values is calculated. There is now a total weighted average TPI on the same 0 to 100 scale indicating the overall TPI of the turf (or crop, land stress, runoff potential, etc.). While the weighted average values are being assessed with much data being collected over the past years and moving forward, the initial formula treats each variable equally. However, here is the weighted average formula written out:

Turf Performance Indicator $W\text{Avg} = \{(100/[(e^{0.5(x-x0/\text{TOL})^2}])\text{TSI } 1*(100/[(e^{0.5(x-x0/\text{TOL})^2}])\text{TSI } 2*(100/[(e^{0.5(x-x0/\text{TOL})}])\text{TSI } 3\}$ etc.

(Weighted valueTSI1+Weighted valueTSI2+Weighted valueTSI3,etc.)

In a first phase, all variables are given equal weight, where n is the number of individual TSI's calculated, the Turf Performance Indicator without weighted averages applied would be:

$$\text{TPI} = \{100/[(e^{0.5(x-xo/\text{TOL})^2}])\text{TSI } 1 + 100/[(e^{0.5(x-xo/\text{TOL})^2}])\text{TSI } 2 + 100/[(e^{0.5(x-xo/\text{TOL})^2}])\text{TSI } 3 + 100/[(e^{0.5(x-xo/\text{TOL})^2}])\text{TSI } \ldots n\}$$

The more TSI's inputted to the calculation, the more representative the calculation will be to include as many influencing variables as possible. A TPI Report is being developed at this time to summarize a report card for multiple TPI's as they relate to turf performance while giving insight to individual 'scores' that will direct attention to any one variable.

The resulting TPI factor of the above combines the results of several variables into a quantitative analysis of the overall performance potential of a system called the Turf Performance Indicator. Despite looking complex at first site, this calculation is very easily implemented utilizing a database such as the turf analysis system 200, and then relay this information in near real time through the turf analysis application and cloud system. The turf analysis device 100 itself is unique so this calculation is truly unique and based upon the value of much recorded data from turf systems around the globe.

From a practical perspective, users can input their tolerances and simply view the TPI at any given time to know where their system is from zone to zone, property to property (in the case of management companies) or from period to period. At no time does a user have to dive into this calculation. The proprietary nature of the calculation is done in the background while the user simply has to input their optimum level and take readings.

The effects of EC and Moisture together have multiple effects that influence turf performance. It is not always enough to simply look at the moisture and salinity levels without understanding the relationship of these to each other. A ratio of EC to moisture, for instance, indicates the concentration of salts to a given amount of water. This may be insightful to understand as a salinity issue besides just having elevated salts in the turf system. A calculation to understand this involves dividing the EC by moisture. Both would have to be in decimal format with moisture being reported as a decimal percentage water fraction volume (i.e. 0.22=22% moisture by water fraction volume (wfv)). Salinity (EC) on the other hand would be reported to 2 decimal places as well but reporting in deciSiemens per meter (dS/m) such as 0.65 dS/m. In this case, our EC/Moisture ratio would be 0.65/0.22=2.95. This is very high indicating a high salinity concentration for a fairly low amount of moisture. Ideally in turf, the ratio should be around 1.00. However, with the increased demand to use reclaimed and effluent water sources on turf in particular, salinity levels are at an all-time high. This ratio must be considered in a turf system to truly understand turf performance levels at any given time.

Another TSI to be considered includes measuring the effects of temperature and moisture together. In particular, as canopy temperature rises above an optimum level, stresses set in that are influenced by that temperature. As moisture climbs above an optimum level, moisture has a particular impact on turf performance as well. However, when both temperature and moisture rise above their optimum levels, the combination of the two can have a much more negative influence on turf performance. To effectively measure this initially, a simple calculation measuring the points away from optimum for both variables combines these results to get a total departure from the two together and indicating the stress that this combination causes.

For example, if an optimum temperature level is 78 degrees F. and the turf is at 88 degrees in the canopy (measured by the turf analysis device 100), a 10 point variance from optimum is recorded. In addition, if the optimum moisture value is 0.25 wfv, or 25% wfv, and a turf value at 0.38, or 38% wfv, then there is a 13 point variance from optimum for moisture. The combined effects of these would be 23 points from optimum. This is one way to measure the effects of the two variables together. More complex forms of this calculation are possible as more and more data is collected from the turf analysis system from turf systems around the world.

Lab Analytics may be used in turf and agronomy applications for understanding soil influences or water, tissue, pathogenic fungi and microbiological influences as well. One particular way to use lab analytics here is to develop a turf analysis, Soil Health Report. In this report, some specific information is ascertained to understand what the optimal levels are for the particular soil being tested. Each turf analysis 'zone' that is identified at a particular property will have different specific conditions only identified by this analysis.

The variables that are recorded may be used in a logarithmic assessment and have applied optimum levels based on user-determined algorithms. These optimum levels drive how far away from optimum the condition is. In addition to this, a Saturation Percentage may be determined indicating how much water an equal part of soil takes to saturate, or reach field capacity. In one embodiment, an ideal condition for a particular soil and for a quality turf surface may be achieved when the user can maintain a moisture percentage (wfv) that is 40% of the saturation percentage. The measurement may be further refined to include a bulk density of the sample which will indicate whether a dense layer exists in the turf system or not. Soil tests may not identify the existence of such a layer despite the fact that these layers are very detrimental to turf systems and have a significant impact on water holding and salinity holding capacities of the turf system as whole. This analysis overcomes these issues. Additional report guidelines are contemplated.

Figure 4:
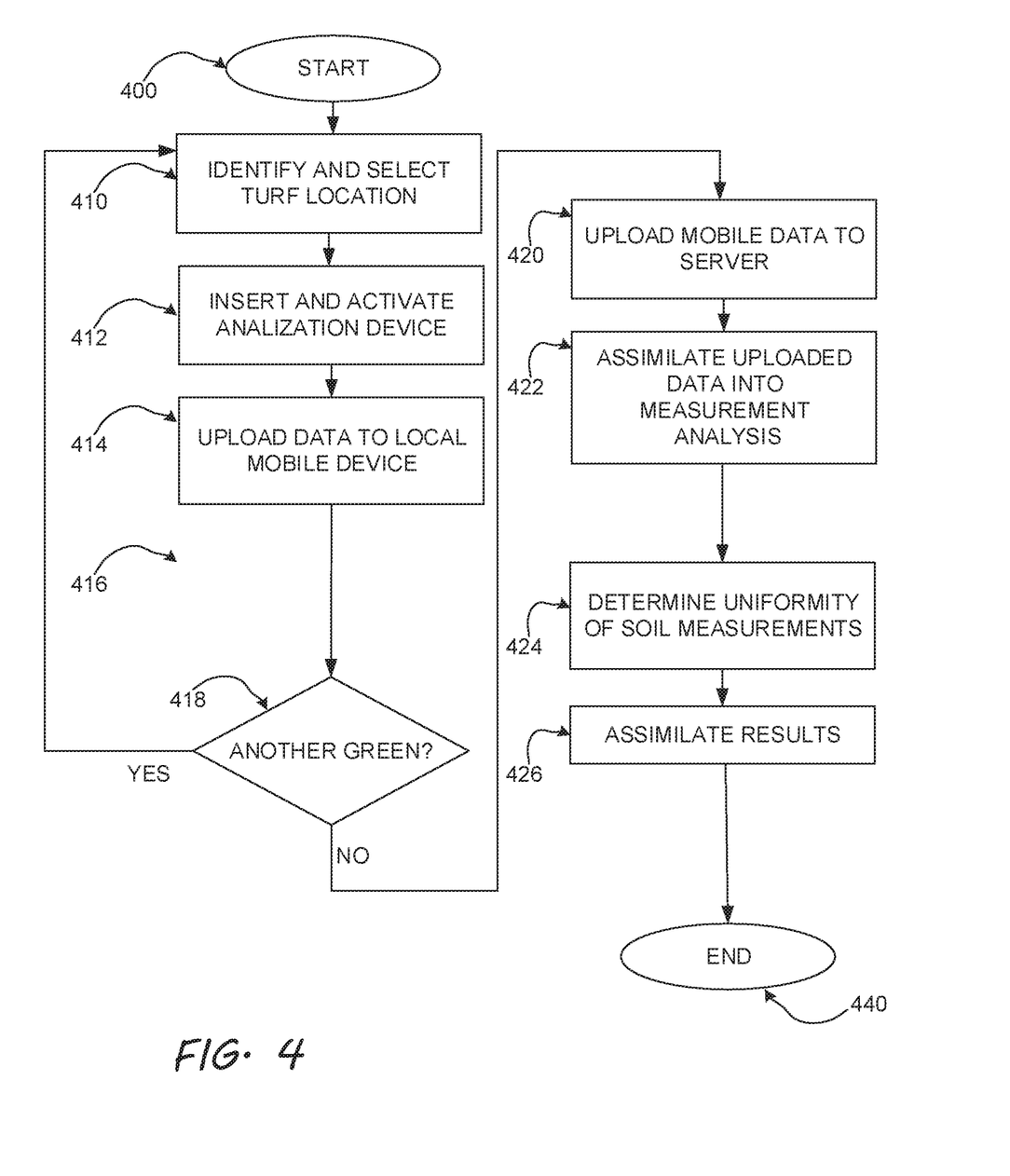
FIG. 4 is a flow chart of a method for determining and using turf quality indicators for water distribution analysis.

FIG. 4 is a flow chart of a method for determining and using turf indicators to determine distribution uniformity of soil measurements, which may include soil moisture, conductivity, salinity, or temperature according to an embodiment of the subject matter discussed herein. The method may start at 400. A user of a turf analysis device 100 may begin collecting field data by identifying and selecting specific turf locations to analyze at 410. Once a turf location is selected, the turf analysis device may be inserted in the turf and activated to determine and collect one or more data points about the underlying turf at 412. At 414, the turf analysis device may store the data collected locally or upload the data to a nearby portable computing device that may be executing a turf analysis application. At 416, the local mobile device may display the collected data measures with the turf analysis device 100 and present the average of soil measurements within the specific turf location to provide an immediate visual indication of the distribution uniformity of the measurements. At 418, a determination is made as to whether additional turf locations are to be analyzed. If yes, the method loops back to 410. If no, the user may proceed to 420.

At 420, the locally collected data may be uploaded to a server computer for further analysis and assimilation. Once uploaded, the data may be used in a series of algorithms at step 422 to determine specific indicators about overall turf quality as discussed above and other factors related to uniformity of soil moisture, soil salinity, soil conductivity, and/or soil temperature. The indicators may then be used to determine an overall water distribution uniformity and uniformity of other measurements in the soil at 424. Then, all indicators determined from direct lab analytics or algorithmic indicators may be assimilated in a set of overall results at 426. Based on the overall results, specific actions may be recommended or taken.

Additional steps may be implemented that utilize additional information such as turf analysis or may discount some data because of anomalies. Further, the steps of the method in FIG. 4 may be implemented in any order and not necessarily the order presented in the embodiment of FIG. 4.

Figure 5:
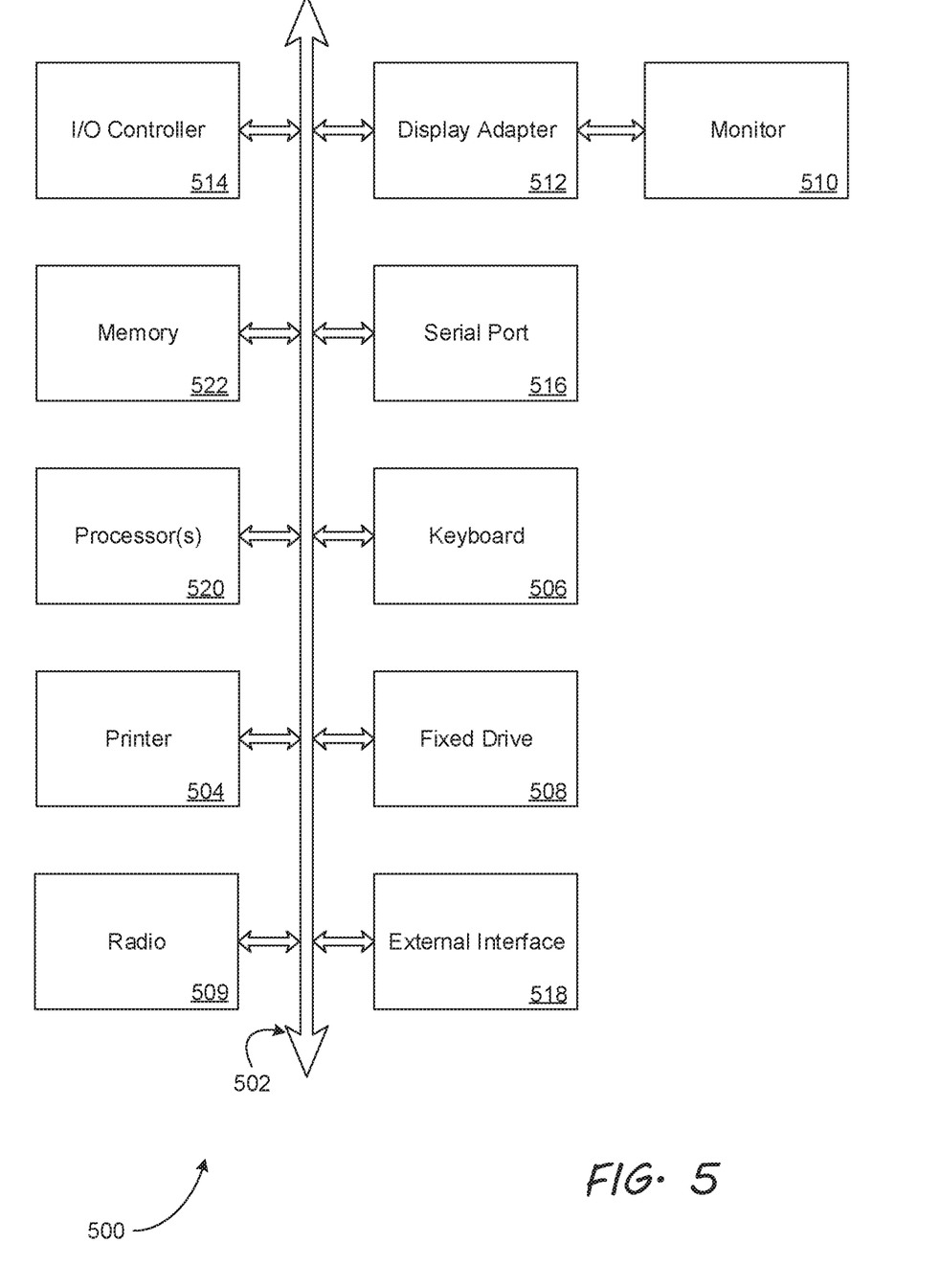
FIG. 5 is a diagram illustrating elements or components that may be present in a computer device or system configured to implement a method, process, function, or operation in accordance with an embodiment of the subject matter disclosed herein.

FIG. 5 is a diagram illustrating various computing elements or components that may be present in a computer device or system 500 configured to implement various computer methods, processes, functions, or operations as discussed above in accordance with various embodiments. The various subsystems shown in FIG. 5 are interconnected via a system bus 502. Additional subsystems may include a printer 504, a keyboard 506, a fixed drive 508, and a monitor 510, which is coupled to a display adapter 512. Peripherals and input/output (I/O) devices, which couple to an I/O controller 514, can be connected to the computer system by any number of means known in the art, such as a serial port 516. For example, the serial port 516 or an external interface 518 can be utilized to connect the computer device 500 to further devices and/or systems not shown in FIG. 5 including a wide area network such as the Internet, a mouse input device, and the like. Communication module may be a radio 509 set to the right frequency to enable communication between the elements and components of the system. The interconnection via the system bus 502 allows one or more processors 520 to communicate with each subsystem and to control the execution of instructions that may be stored in a system memory 522 and/or the fixed drive 508, as well as the exchange of information between subsystems. The system memory 522 and/or the fixed drive 508 may embody a tangible computer-readable medium.

It should be understood that the present disclosures as described above can be implemented in the form of control logic using computer software in a modular or integrated manner. Based on the disclosure and teachings provided herein, a person of ordinary skill in the art will know and appreciate other ways and/or methods to implement the present disclosure using hardware and a combination of hardware and software.

Any of the software components, processes or functions described in this application may be implemented as software code to be executed by a processor using any suitable computer language such as, for example, Java, Javascript, C++, PHP, or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

All references, including publications, patent applications, and patents, cited herein are hereby incorporated by reference to the same extent as if each reference were individually and specifically indicated to be incorporated by reference and/or were set forth in its entirety herein.

The use of the terms "a" and "an" and "the" and similar referents in the specification and in the following claims are to be construed to cover both the singular and the plural, unless otherwise indicated herein or clearly contradicted by context. The terms "having," "including," "containing" and similar referents in the specification and in the following claims are to be construed as open-ended terms (e.g., meaning "including, but not limited to,") unless otherwise noted. Recitation of ranges of values herein are merely indented to serve as a shorthand method of referring individually to each separate value inclusively falling within the range, unless otherwise indicated herein, and each separate value is incorporated into the specification as if it were individually recited herein. All methods described herein can be performed in any suitable order unless otherwise indicated herein or clearly contradicted by context. The use of any and all examples, or exemplary language (e.g., "such as") provided herein, is intended merely to better illuminate embodiments and does not pose a limitation to the scope of the disclosure unless otherwise claimed. No language in the specification should be construed as indicating any non-claimed element as essential to each embodiment of the present disclosure.

Different arrangements of the components depicted in the drawings or described above, as well as components and steps not shown or described are possible. Similarly, some features and sub-combinations are useful and may be employed without reference to other features and sub-combinations. Embodiments have been described for illustrative and not restrictive purposes, and alternative embodiments will become apparent to readers of this patent. Accordingly, the present subject matter is not limited to the embodiments described above or depicted in the drawings, and various embodiments and modifications can be made without departing from the scope of the claims below.

What is claimed is:

1. A method, comprising:
   inserting a portion of a turf analysis device into turf at a plurality of locations, each inserting proximate in time with respect to each other inserting and each insertion penetrating a canopy of turf to reach a portion of turf just below the canopy, the turf analysis device including a portion that penetrates a surface of the turf and a portion that remains above the surface of the turf;
   collecting data about one or more conditions of the turf just below the canopy substantially simultaneous with the inserting of the turf analysis device at a plurality of locations proximate in time in a golf course using the turf analysis device;
   assimilating the collected data proximate in time to a database of a computing device communicating with the turf analysis device;
   applying the collected turf condition data into a distribution algorithm; and
   calculating one or more turf indicators to determine the distribution uniformity of the plurality of turf locations in the golf course using a logarithmic relationship of the collected data to a known tolerance value compared to a target value; and
   analyzing the collected data at the plurality of locations to determine distribution uniformity of the turf just below the canopy across the plurality of turf locations in the golf course with respect to a time span associated with the proximate times of the insertions.

2. The method of claim 1, further comprising:
   in response to calculating the one or more turf indicators, assessing at least one of turf performance and turf stress of the plurality of turf locations in the golf course.

3. The method of claim 1, further comprising:
   collecting location data corresponding to the plurality of turf locations in the golf course; and
   linking the collected turf condition data to the database of the computing device based on the collected location data.

4. The method of claim 1, further comprising:
   sensing the data about the one or more conditions of turf through one or more sensors of the turf analysis device;
   logging the sensed data of the one or more conditions; and
   storing the sensed data to the database of the computing device.

5. The method of claim 1, wherein the turf analysis device further configured to log information comprising at least one of the group comprised of: date, time, latitude, longitude, altitude, picture, and electronic notes.

6. The method of claim 1, wherein the one or more conditions comprises at least one of the group comprised of: moisture, electric conductivity, soil salinity, humidity, and temperature.

7. A system, comprising:
   a server computer having a database configured to store data corresponding to a plurality of turf locations in a golf course;
   a portable turf analysis device having a first end configured to penetrate a surface of turf to reach just below a canopy of the turf and a second end coupled to the first end and configured to remain disposed away from the surface of the turf, the turf analysis device communicatively coupled to the server computer and configured to collect data for one or more turf conditions just below the canopy for each of the plurality of turf locations in the golf course substantially simultaneous with each penetration, each data collection proximate in time with respect to each other data collection and configured to communicate the proximate-time collected data to the server computer simultaneous with each penetration; and
   an analysis module executable on the server computer and configured to assimilate the proximate-time collected data received from the turf analysis device and to apply the collected turf condition data into a distribution algorithm and calculate one or more turf indicators using a logarithmic relationship of the collected data to a known tolerance value compared to a target value to determine distribution uniformity of the turf just below the canopy across the plurality of turf locations in the golf course in response to receiving the collected data.

8. The system of claim 7, further comprising a remote computing device communicatively coupled to the turf analysis device, the remote computing device configured to receive global position data collected from the turf analysis device and to send the global position data to the server computer.

9. The system of claim 7, further comprising a local computing device communicatively coupled to the server computer and configured to display the collected data.

10. The system of claim 7, wherein the server computer is further configured to execute the analysis module to assess at least one of turf performance and turf stress of the plurality of turf locations in the golf course in response to determining a turf performance indicator.

11. The system of claim 7, further comprising:
    one or more sensors connected to the turf analysis device and configured to sense the data about the one or more turf conditions; and
    the server computer further configured to log and store the sensed data.

12. The system of claim 7, wherein the one or more conditions comprises at least one of the group comprised of: moisture, electric conductivity, soil salinity, humidity, and temperature.

13. The system of claim 7, wherein the turf analysis device further configured to log information comprising at least one of the group comprised of: date, time, latitude, longitude, altitude, picture, and electronic notes.

* * * * *